United States Patent [19]
Baroni et al.

[11] Patent Number: 5,447,931
[45] Date of Patent: Sep. 5, 1995

[54] NEW THERAPEUTIC USE OF HETEROCYCLPIPERAZINES AS 5-HT$_3$ AGONISTS AND NEW COMPOUNDS

[75] Inventors: Marco Baroni, Vanzago; Umberto Guzzi; Antonina Giudice, both of Milan; Marco Landi, Bussero, all of Italy

[73] Assignee: Sanofi, Paris, France

[21] Appl. No.: 344,629

[22] Filed: Nov. 17, 1994

Related U.S. Application Data

[63] Continuation of Ser. No. 81,132, Jun. 25, 1993, abandoned.

[30] Foreign Application Priority Data

Jun. 25, 1992 [EP]  European Pat. Off. ............ 92401800

[51] Int. Cl.$^6$ .................. A61K 31/495; C07D 401/04; C07D 403/04; C07D 241/02
[52] U.S. Cl. .................. 514/252; 544/360; 544/295; 544/357
[58] Field of Search .................. 544/360; 514/252

[56] References Cited

U.S. PATENT DOCUMENTS

| | | | |
|---|---|---|---|
| 2,562,036 | 7/1951 | Hultquist et al. | 544/360 |
| 2,606,906 | 8/1952 | Hultquist et al. | 544/360 |
| 4,078,063 | 3/1978 | Lumma, Jr. et al. | 544/360 |
| 4,081,542 | 3/1978 | Lumma, Jr. et al. | 544/360 |
| 4,163,849 | 8/1979 | Lumma, Jr. et al. | 544/357 |
| 4,442,103 | 4/1984 | Saari | 544/360 |

FOREIGN PATENT DOCUMENTS

| | | |
|---|---|---|
| 1451232 | 7/1966 | France . |
| 2539990 | 8/1984 | France . |
| WO88/07528 | 10/1988 | WIPO . |
| WO92/02518 | 2/1992 | WIPO . |

OTHER PUBLICATIONS

Cignarella et al., *Farmaco Ed. Sci.*, 34(9), 1979, pp. 817–823.
Regnier et al., *J. Med. Chem.* 11(6), 1968, 1151–1155.
Saari et al., *J. Med. Chem.*, 26(12), 1983, 1696–1701.
Croci et al., *J. Pharm. Pharmacol.*, 44(4), 1992, 358–360.
Patel et al., *Indian J. Physiol. Pharmacol.* 25(4), 1981, 379–384.
*Phychopharmacol. Bull.* 27(2), 1991, 163–170.
Bianchi et al., *Eur. J. Pharmacol.*, 147(3), 1988, 343–350.
Bianchi et al., *Eur. J. Pharmacol.* 151(3), 1988, 365–371.
Glennon et al., *Eur. J. Pharmacol.*, 168(3), 1989, 387–392.

*Primary Examiner*—Cecilia Tsang
*Attorney, Agent, or Firm*—Bacon & Thomas

[57]  ABSTRACT

New therapeutic use of some heterocyclylpiperazines of formula (I)

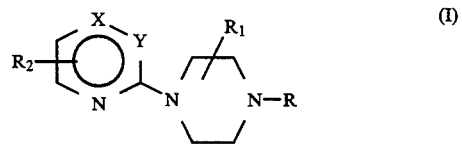

wherein R represents hydrogen or (C$_1$–C$_4$)alkyl, R$_1$ represents hydrogen or a methyl group, R$_2$ represents hydrogen or a halogen atom; X et Y represent each —CH=, or one is —CH= and the other is —N=, as well as their pharmaceutically acceptable salts for the preparation of a medicament for the treatment or prophylaxis of the pathological conditions which can be improved by 5-HT$_3$ mediated selective agonism and new compounds deriving from this chemical class.

5 Claims, No Drawings

NEW THERAPEUTIC USE OF HETEROCYCLPIPERAZINES AS 5-HT₃ AGONISTS AND NEW COMPOUNDS

This application is a Continuation of application Ser. No. 08/081,132, filed Jun. 25, 1993, now abandoned.

The present invention concerns a new therapeutic use of some heterocyclylpiperazines and new compounds deriving from this chemical class. U.S. Pat. No. 4,078,063 and EP patent 65 757 describe some 2-piperazinylpyridines, in which the pyridine ring is substituted by a halogen atom, as anorectic, antidepressant and anti-hypertensive agents. U.S. Pat. No. 4,163,849 and BE patent 840 904 describe some 6-chloro-2-piperazinylpyrazines, wherein the piperazine ring is optionally 4-substituted by an alkyl group, as anorectic agents. Some 2-piperazinylpyrimidines are described in DE patent 3 507 983 as synthesis intermediates. Eur. J. Pharmacol. 168, No. 3, 387-392, 1989, describes some binding studies of arylpiperazines to 5-HT₃ receptors but no indication is given whether the tested compounds are agonists or antagonists.

It has now been found that some heterocyclylpiperazines are selective and potent 5-HT₃ agonists.

The present invention concerns therefore the use of at least one heterocyclylpiperazine of formula (I) for the preparation of a medicament for the treatment or prophylaxis of pathologies deriving from disorders of the serotoninergic system, wherein a serotoninergic action selectively mediated by 5-HT₃ receptors is considered to be beneficial. A first object of the present invention is therefore a method for treating a mammal suffering from or susceptible to a condition which can be improved or prevented by the serotonin 5-HT₃ receptors agonism which comprises administering to said mammal an effective amount of at least a compound of formula (I)

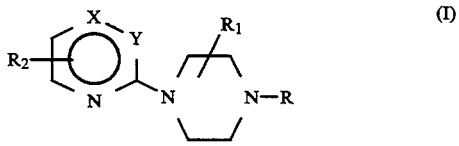

wherein R represents hydrogen or (C₁-C₄)alkyl, R₁ represents hydrogen or a methyl group, R₂ represents hydrogen or a halogen atom; X et Y represent each —CH=, or one is —CH= and the other is —N=, or of a pharmaceutically acceptable salt thereof. In the present invention the term "(C₁-C₄)alkyl" designates a saturated aliphatic hydrocarbon residue of 1, 2, 3 or 4 carbon atoms, namely methyl, ethyl, propyl, isopropyl, n-butyl, iso-butyl, sec-butyl, tert-butyl; the term "halogen" designates the four common halogens chloro, fluoro and bromo being particularly preferred; the ring containing X and Y, which are defined as above, forms a pyridine, a pyrimidine or a pyrazine ring.

The addition salts of the compounds of formula (I) with physiologically acceptable acids, are part of the present invention.

The physiologically acceptable salts comprise the addition salts with mineral or organic physiologically acceptable acids, such as hydrochlorides, hydrobromides, sulfates, phosphates, acetates, tartrates, succinates, maleates, fumarates, mesylates, tosylates and the like salts.

Compounds of formula (I) may be easily prepared by a general method which comprises reacting a piperazine of formula (II)

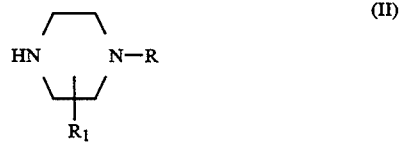

with an heteroaromatic ring of formula (III)

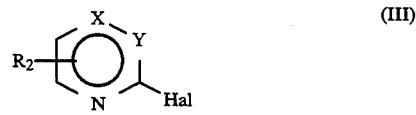

wherein Hal represents a halogen atom and R, R₁, R₂, X and Y are defined as above.

The reaction is generally made by mixing compounds (II) and (III) in a suitable solvent, the temperature ranging from room temperature to 200° C., according to the solvent and the reaction time.

A more detailed description of the general process is described in the above cited U.S. Pat. No. 4,078,063, EP 65757, U.S. Pat. No. 4,163,849, BE 840904 and DE 3507983.

The affinity of the compounds of formula (I) for 5-HT₃ receptors has been evaluated by means of an in vitro binding test using binding sites in the rat cerebral cortical tissue (cfr. G. J. Kilpatrick, B. J. Jones and M. B. Tyers—Identification and distribution of 5-HT₃ receptors in rat brain using radioligand binding—Nature, 1987, 330,746-8) and [3H] BRL 43694 (granisetron), a potent and specific 5-HT₃ receptor antagonist.

The membrane preparation and the binding test were carried out according to the method described by Nelson and Thomas (D. R. Nelson and D. R. Thomas—[³H] BRL 43694 (Granisetron), a specific ligand for 5-HT₃ binding sites in rat brain cortical membranes. Biochem. Pharmacol., 1989, 38, 1963-5). The results were calculated by means of non-linear fitting methods "Accufit saturation" for the saturation studies (H. A. Feldman—Mathematical theory of complex ligand-binding systems at equilibrium: some methods of parameter fitting— Analyt.Biochem., 1972, 48, 317-38) and "Accufit competition" for the displacing studies (H. A. Feldman, D. Rodbord, and D. Levine—Mathematical theory of cross reactive radioimmunoassay and ligand-binding systems at equilibria—Analyt.Biochem., 1972, 45, 530-56).

In order to evaluate the affinity of the tested compounds, 0,5 nM concentration of [³H] BRL 43694 was used.

The compounds of :formula (I) showed to be generally more potent than serotonin and 2-methylserotonin in displacing [3H] BRL 43694. 5-HT₃ affinity and selective agonism of compounds of formula (I) was confirmed by studies in the anesthetized rat; in this test, intravenous administration of the compound shows a short-lives reduction of heart rate (Bezold-Jarisch effect), the intensity varying depending on the dose and being comparable to that obtained by administering serotonin or 2-methylserotonin.

This effect is inhibited by selective 5-HT₃ receptor antagonists (e.g. ICS 205-930 also known as tropisetron and zacopride), while it is not inhibited by serotonin D receptor antagonists (e.g. methysergide).

More particularly, the Bezold-Jarisch effect evoked by the compounds of formula (I) was evaluated using Sprague-Dawley rats weighing from 200 to 300 g, anaesthetised with urethane 1.25 g/kg i.p.. The blood pressure was recorded from the carotid artery and heart rate was evaluated, as pulse frequency, by means of a cardiotachometer. A catheter was inserted into the jugular vein for the administration of the substances.

Different doses of the compounds to be tested were administered intravenously in a volume of 0.5 ml/kg.

Bradycardia provoked by each single dose is expressed as percentage of the basal heart rate; the $ID_{50}$, i.e. the dose which inhibits by 50% the heart rate in the treated animals, is thus calculated.

In this test the compounds of formula (I) showed $ID_{50}$ ranging from 0.5 to 10 µg/kg.

As far as 5-$HT_3$ mediated agonism is concerned, 6-chloro-2-piperazinylpyridine, 6-chloro-2-(4-methylpiperazinyl)pyridine, 6-bromo-2-(4-methylpiperazinyl)pyridine and 6-chloro-2-(3-methylpiperazinyl)pyridine and the pharmaceutically acceptable salts thereof are particularly interesting compounds.

Thanks to their potent activity related to 5-$HT_3$ receptors and to their low toxicity, the compounds of formula (I) may be useful as medicaments for the treatment of those pathologies related to the disorders of the serotoninergic system at peripheral or central level.

In general the above compounds may be employed in the treatment of all pathological conditions wherein a serotonin-like action selectively mediated by the 5-$HT_3$ receptors may be beneficial.

More particularly compounds of formula (I) may be used in the treatment of dysthymic disorders, anxiety or psychotic troubles.

The above compounds may also be employed for the treatment of intestinal motility troubles and in particular in the treatment of constipation.

Intestinal prokinetic activity was investigated by subjecting the compounds of formula (I) to a test aimed at evaluating fecal excretion in rats. Said test was carried out according to the experimental method described in EP 412 901.

Results are expressed in [IA-1g], which represents the activity index indicating the dose effective to stimulate 1 g fecal excretion (dry weight).

In this test the compounds of formula (I) showed a good activity, the results, expressed in [IA-1g], ranging from. 0.5 to 3 mg/kg.

For their therapeutical use, the compounds of formula (I), as well as their pharmaceutically acceptable salts, pure or in combination with any other pharmaceutically compatible substance, may conveniently be administered orally, parenterally, sublingually, rectally or transdermally, suitably formulated in pharmaceutical compositions.

For oral administration, suitable pharmaceutical dosage forms comprise tablets, capsules, granules or liquid compositions as syrups, solutions, emulsions, suspensions etc.

For parenteral administration, sterile injectable aqueous or not aqueous solutions may be used, conventional suppositories can be employed for rectal administration, patches for transdermal administration; when necessary, sustained release forms may be prepared as well as pharmaceutical compositions in which the active principle of formula (I) is included in lyposomes or cyclodextrins.

The pharmaceutical compositions are prepared according to conventional methods, mixing the active principle of formula (I) with the excipients and additives conventionally employed in the pharmaceutical practice, such as starch, lactose, saccharose, magnesium stearate, animal or vegetal fats, glycols, paraffin derivatives, wetting, dispersing, emulsifying, preservative agents and the like.

The amount of active principle to be daily administered will depend on the particular therapeutical indication, on the severity of the pathology to be treated as well as on the age, and weight of the patient and the administration route.

In general for this new therapeutic use, the daily dosage varies between 0.05 and 100 mg, and preferably between 0.1 and 50 mg, optionally divided in fractionated doses to be administered more times a day, preferably from 1 to 3 times a day.

Unit dosage forms for the new therapeutic use will typically comprise from 0.05 to 20 mg, preferably from 0.1 to 10 mg, including for instance 0.5 to 5 mg (e.g. 0.5, 1, 1.5, 2, 2.5, 3, 3.5, 4, 4.5, 5 mg) of active principle. These unit dosage forms are typically administered one or more times a day, preferably from 1 to 3 times a day.

| | |
|---|---|
| 6-bromo-2-(4-methylpiperazinyl)pyridine | 5 mg |
| lactose | 50 mg |
| talc | 44 mg |
| magnesium stearate | 1 mg |

A further object of the present invention is the new heterocyclylpiperazines of formula (I):
the 6-chloro-2-(3-methylpiperazinyl)pyridine and the pharmaceutically acceptable salts thereof;
the 6-chloro-2-(4-methylpiperazinyl)pyridine and the pharmaceuticeutically acceptable salts thereof;
the 6-bromo-2-(4-methylpiperazinyl)pyridine and the pharmaceutically acceptable salts thereof.

The said new heterocyclylpiperazines are prepared as indicated on page 2 of the present specification. Their preparation is illustrated in the below examples.

The present invention also concerns a pharmaceutical composition which contains as the active principle, at least one of the new compounds listed above in its basic form or an addition salt thereof with a physiologically compatible acid.

EXAMPLE 1

6-chloro-2-(4-methylpiperazinyl)pyridine hydrochloride

To a solution of 7.5 g (0.05 mol) of 2,6-dichloropyridine in 70 ml of DMSO, 6.9 g (0.05 tool) of anhydrous $K_2CO_3$ and 5.5 ml (0.05 tool) of N-methyl piperazine are added. The mixture is stirred at 80° C. for 4 hours, then poured into ice/water and extracted with ethyl acetate, dried over $Na_2SO_4$, filtered and the solvent is evaporated off. The residue is dissolved in 30 ml of hydrogen chloride saturated isopropanol. The precipitate is collected by filtration and recrystallized from isopropanol to provide 4.8 g of a white powder. M.p. 225°–227° C. For a better purification, the above product is dissolved in a diluited solution of NaOH, extracted with ethyl acetate, the organic phase is washed with water, stirred for 10 min. with some silica gel, dried over Na$_2$SO$_4$, filtered and the solvent is evaporated off.

The hydrochloride salt is reprepared to provide 1.5 g of the compound of the title. M.p. 233°–235° C.

EXAMPLE 2

6-bromo-2-(4-methylpiperazinyl)pyridine hydrochloride

A mixture of 11.84 g (0.05 mol) of 2,6-dibromopyridine, 70 ml of DMSO, 6.9 g (0.05 tool) of anhydrous K$_2$CO$_3$ and 5.5 ml (0.05 tool) of N-methylpiperazine are stirred at 80° C. for 4 hours. The mixture is then poured in ice/water, extracted with ethyl acetate, dried over Na$_2$SO$_4$, filtered and the solvent is evaporated off. The residue is dissolved in 30 ml of ethyl ether and stirred for 10 min with some silica gel, dried over Na$_2$SO$_4$, filtered and the solvent is evaporated off. The hydrochloride salt is prepared by means of hydrogen chloride saturated isopropanol, to provide 8.7 g of crude product which is recrystallized from ethanol 95% to give 7 g of the compound of the title. M.p. 273°–275° C.

EXAMPLE 3

6-chloro-2-(3-methylpiperazinyl)pyridine a) 1-benzyl-3-methylpiperazine

To 500 ml of ice cooled methyl ethyl ketone, 126.5 g (1 mol) of benzyl chloride, 100 g (1 mol) of 2-methylpiperazine, 138 g (1 mol) of anhydrous K$_2$CO$_3$ and 2 g of NaI are added. The mixture is stirred at the reflux temperature for 2 hours, then cooled to room temperature; K$_2$CO$_3$ is filtered off and the solvent evaporated. The residue is dissolved in diluted NaOH, extracted with some ethyl ether, washed with water, dried over Na$_2$SO$_4$ and the solvent is evaporated off to provide 55 g of 1-benzyl-3-methylpiperazine. B.p. 140°–150° C./20–25 mmHg.

b) 1-benzyl-4-formyl-3-methylpiperazine

A mixture of 54 g (0.28 mol) of the compound obtained in the step a) above and 10.7 ml (0.28 mol) of 99% formic acid is stirred at 180° C. for 4 hours; the mixture is then distilled to give 52.5 g of 1-benzyl-4-formyl-3-methylpiperazine. B.p. 145° C./0.05 mmHg.

c) 1-formyl-2-methylpiperazine

To a solution of 51 g (0.23 mol) of compound (4) in 300 ml of absolute ethanol, 6 g of Pd/C 10% are added. The mixture is hydrogenated at atmosphere pressure, heating at 35°–40° C. The reaction may be easily followed by T.L.C. and once completed, about 6 hours later, the catalyst is filtered off and the solvent evaporated to provide an oil which is distilled to give 23 g of 1-formyl-2-methylpiperazine. B.p.95° C./0.3 mmmHg.

d) 6-chloro-2-(4-formyl-3-methylpiperazinyl)pyridine

A mixture of 20.5 g (0.138 mol) of 2,6-dichloropyridine, 19.1 g (0.138 mol) of K$_2$CO$_3$, 21.5 g (0.155 tool) of the compound obtained above in step c), in 140 ml of xylene are stirred at the reflux temperature for 14 hours; the mixture is then cooled to room temperature and some ethyl ether is added. The suspension is washed with water then with diluted HCl, dried over Na$_2$SO$_4$, filtered and the solvent is evaporated. The residue is dissolved in ethyl ether and extracted with 2N HCl. The two phases are separated and the aqueous phase is alkalinised then extracted with ethyl ether, washed with water, dried over Na$_2$SO$_4$, filtered and the solvent is evaporated to give 14 g of the desired compound.

e) 6-chloro-2-(3-methylpiperazinyl)pyridine hydrochloride 14 g (0.058 mol) of the compound obtained above in the step d), in 200 ml of 2N HCl are stirred at the reflux temperature for 1 hour. The mixture is then cooled to room temperature, washed with ethyl ether, alkalinised with diluted NaOH, extracted with ethyl ether and dried over Na2SO$_4$. After filtration the hydrochloride salt is prepared by the addition of hydrogen chloride saturated isopropanol to provide 8 g of the compound of the title. M.p. 209°–212° C.

Elemental analysis: calc.: N$_{basic}$11,28% Cl$_{tot}$28,57% found: N$_{basic}$11,27% Cl$_{tot}$29,41%.

We claim:

1. 6-Bromo-2-(4-methylpiperazinyl)pyridine and pharmaceutically acceptable addition salts thereof.

2. 6-Bromo-2-(4-methylpiperazinyl)pyridine hydrochloride.

3. A pharmaceutical composition comprising an effective amount of at least one compound according to claim 1 in admixture with a pharmaceutical carrier.

4. A pharmaceutical composition comprising an effective amount of the compound according to claim 2 in admixture with a pharmaceutical carrier.

5. A pharamaceutical composition according to claim 3 which further comprises 6-bromo-2-(4-methylpiperazinyl)pyridine hydrochloride.

* * * * *